United States Patent
Ilan et al.

(10) Patent No.: US 10,464,998 B2
(45) Date of Patent: Nov. 5, 2019

(54) ANTI-LPS ENRICHED IMMUNOGLOBULIN FOR USE IN TREATMENT AND/OR PROPHYLAXIS OF FIBROSIS

(71) Applicant: HADASIT MEDICAL RESEARCH SERVICES AND DEVELOPMENT LIMITED, Jerusalem (IL)

(72) Inventors: Yaron Ilan, Jerusalem (IL); Meir Mizrahi, Modi'in (IL)

(73) Assignee: HADASIT MEDICAL RESEARCH SERVICES AND DEVELOPMENT LIMITED, Jerusalem (IL)

( * ) Notice: Subject to any disclaimer, the term of this patent is extended or adjusted under 35 U.S.C. 154(b) by 0 days.

(21) Appl. No.: 15/033,485

(22) PCT Filed: Oct. 29, 2014

(86) PCT No.: PCT/IB2014/065676
§ 371 (c)(1),
(2) Date: Apr. 29, 2016

(87) PCT Pub. No.: WO2015/063693
PCT Pub. Date: May 7, 2015

(65) Prior Publication Data
US 2016/0251414 A1 Sep. 1, 2016

(30) Foreign Application Priority Data
Oct. 30, 2013 (AU) .................................. 2013904191

(51) Int. Cl.
| | | |
|---|---|---|
| *A61K 39/395* | (2006.01) | |
| *C07K 16/12* | (2006.01) | |
| *A61K 35/20* | (2006.01) | |
| *G01N 33/68* | (2006.01) | |
| *G01N 33/52* | (2006.01) | |
| *A61K 39/00* | (2006.01) | |

(52) U.S. Cl.
CPC .......... *C07K 16/1203* (2013.01); *A61K 35/20* (2013.01); *G01N 33/52* (2013.01); *G01N 33/6893* (2013.01); *A61K 2039/505* (2013.01); *C07K 2317/12* (2013.01); *C07K 2317/20* (2013.01); *C07K 2317/76* (2013.01); *G01N 2800/085* (2013.01); *G01N 2800/7052* (2013.01)

(58) Field of Classification Search
CPC ................................................ C07K 16/1203
See application file for complete search history.

(56) References Cited

U.S. PATENT DOCUMENTS

2011/0200610 A1* 8/2011 Ilan .................... A61K 39/395
424/158.1

FOREIGN PATENT DOCUMENTS

| WO | WO 2003/080082 A1 | 10/2003 |
|---|---|---|
| WO | WO 2004/078209 A1 | 9/2004 |
| WO | WO 2006/053383 A1 | 5/2006 |
| WO | WO 2010/125565 A2 | 11/2010 |
| WO | WO 2015/063693 A1 | 5/2015 |

OTHER PUBLICATIONS

Adar et al., "Oral administration of immunoglobulin G-enhanced cotostrum alleviates insulin resistance and liver injury and is associated with alterations in natural killer T cells," *Clinical & Experimental Immunology* 167(2):252-260 (2012).
De Minicis et al. "Dysbiosis Contributes to Fibrogenesis in the Course of Chronic Liver Injury in Mice," *Hepatology* 59(5):1738-1749 (2013).
Gómez-Hurtado et al., "Gut Microbiota Dysbiosis is Associated with Inflammation and Bacterial Translocation in Mice with $CCl_4$-Induced Fibrosis," *PLoS One* 6(7):e23037 (2011) (10 pgs.).
Guarner et al., "The detection of bacterial DNA in blood of rats with $CCl_4$-induced cirrhosis with ascites represents episodes of bacterial translocation," *Hepatology*, 44(3):633-639 (2006).
Liu et al., "Kupffer cells are associated with apoptosis, inflammation and fibrotic effects in hepatic fibrosis in rats," *Lab Invest.* 90(12):1805-1816 (2010).
Ma et al., "Histopathologic Evaluation of Liver Biopsy for Cirrhosis," *Adv. Anat. Pathol.* 19(4):220-230 (2012).
*Remington's Pharmaceutical Sciences*, Gennaro A. R. ed., Mack Publishing Co., Easton, PA, pp. 1521-1712 (1990).
Wiest et al., "Pathological bacterial translocation in liver cirrhosis," *J. Hepatology*, vol. 60, pp. 197-209 (2014).
European Patent Office, International Search Report in International Application No. PCT/IB2014/065676 (dated Apr. 7, 2015).
European Patent Office, Written Opinion in International Application No. PCT/IB2014/065676 (dated Apr. 7, 2015).
International Bureau of WIPO, International Preliminary Report on Patentability in International Application No. PCT/IB2014/065676 (dated May 3, 2016).

* cited by examiner

*Primary Examiner* — Albert M Navarro
(74) *Attorney, Agent, or Firm* — Browdy and Neimark, PLLC

(57) ABSTRACT

This invention relates to methods and compositions for treating fibrosis, by administering compositions comprising anti-LPS immunoglobulin enriched colostrum preparations. In particular, the invention relates to methods and compositions for the treatment of liver fibrosis and/or lung fibrosis. Prophylactic or therapeutic compositions and diagnostic methods are also disclosed and claimed.

6 Claims, 13 Drawing Sheets

* p<0.0002
** p<0.001

Group A

Group B

Group C

Group A

Group B

Group C

ANTI-LPS ENRICHED IMMUNOGLOBULIN FOR USE IN TREATMENT AND/OR PROPHYLAXIS OF FIBROSIS

CROSS-REFERENCE TO RELATED APPLICATIONS

This patent application is the U.S. national phase of International Patent Application No. PCT/IB2014/065676, filed on Oct. 29, 2014, which claims the benefit of Australian Provisional Patent Application number 2013904191, filed 30 Oct. 2013, the disclosures of which are incorporated herein by reference in their entireties for all purposes.

FIELD OF THE INVENTION

This invention relates to methods and compositions for the treatment or alleviation of fibrosis and closely related conditions. In particular, the invention relates to methods and compositions for the treatment of lung fibrosis or liver fibrosis.

BACKGROUND OF THE INVENTION

Fibrosis is an intrinsic response to chronic injury, maintaining organ integrity when extensive necrosis or apoptosis occurs. With protracted damage, fibrosis can progress toward excessive scarring and organ failure, as in liver cirrhosis.

Liver fibrosis is the common scarring reaction associated with chronic liver injury that results from prolonged parenchymal cell injury and/or inflammation. The fibrogenic response is characterized by progressive accumulation of extracellular matrix components enriched in fibrillar collagens and a failure of matrix turnover. This process is driven by a heterogenous population of hepatic myofibroblasts that mainly derive from hepatic stellate cells and portal fibroblasts. Hepatic stellate cells are liver-specific mesenchymal cells that play vital roles in liver physiology and fibrogenesis. They are located in the space of Disse and maintain close interactions with sinusoidal endothelial cells and hepatic epithelial cells. It is becoming increasingly clear that hepatic stellate cells have a profound impact on the differentiation, proliferation, and morphogenesis of other hepatic cell types during liver development and regeneration.

Some studies suggest that regression of fibrosis can be achieved by the successful control of the cause of the chronic liver injury, owing to termination of the fibrogenic reaction following clearance of hepatic myofibroblasts and restoration of fibrolytic pathways, such as during anti viral therapy targeting hepatitis B and C viruses.

While mild fibrosis remains largely asymptomatic, its progression toward cirrhosis, i.e., replacement of functional parenchyma by scar tissue accompanied by severe architectural and vascular distortion, is the major cause of liver-related morbidity and mortality. Moreover, numerous patients present initially in the clinic with advanced fibrosis or cirrhosis, which are largely irreversible. Therefore, antifibrotics that prevent progression toward cirrhosis or induce regression of fibrosis and cirrhosis are urgently needed.

Idiopathic pulmonary fibrosis (IPF) is a progressively fibrotic interstitial lung disease that is associated with a median survival of 2-3 years from initial diagnosis. Specifically, IPF is no longer thought to be a predominantly pro-inflammatory disorder. Rather, the fibrosis in IPF is increasingly understood to be the result of a fibroproliferative and aberrant wound healing cascade.

In addition, fibrosis of any other organ including heart, muscle, kidneys, pancreas, bowel, and others is the final common pathway for many disorders—many of which do not necessarily involve the immune system in their pathogenesis.

While some drugs effective against other known causes of fibrosis, such as chronic viral hepatitis B or C, autoimmune and biliary diseases, alcoholic steatohepatitis (ASH) or nonalcoholic steatohepatitis (NASH) may exert some anti fibrotic effect, most of them are more effective in preventing the deterioration of the process rather than actually reversing an existing fibrotic state. Moreover, for many of the liver disorders, as well as other organs, the exact cause of the disease is unknown, and therefore there are not targets for therapy. For these cases, a direct anti fibrotic compound is required.

Understanding of the complex network underlying liver fibrogenesis has allowed the identification of a large number of antifibrotic targets, but no antifibrotic drug has as-yet been approved. To date, antifibrotic treatment of fibrosis represents an unconquered area for drug development. Preclinical research has yielded numerous targets for antifibrotic agents, some of which have entered early-phase clinical studies, but progress has been hampered due to the relative lack of sensitive and specific biomarkers to measure fibrosis progression or reversal.

Whilst it may be expected that known anti-inflammatory drugs would by course also reduce fibrosis in a target organ, such anti-inflammatory drugs have not proven effective in this disease.

Many anti-inflammatory agents failed in alleviating fibrosis, suggest that additional pathways, some that are not yet identified, are involved in the process.

We hypothesise that the molecular pathways that lead to fibrosis are of higher complexity than originally anticipated and separate from those pathways which are related to inflammation in the relevant organ. Also in some organs, activation of inflammatory pathways may only one of many building blocks in the process of inducing fibrosis, and therefore, an anti-inflammatory compound is not sufficient for stopping the process.

SUMMARY OF THE INVENTION

In a first aspect, the invention provides a method of prophylaxis, treatment and/or alleviation of fibrosis in a subject, comprising the step of administering to the subject a therapeutically effective amount of a composition comprising an anti-LPS immunoglobulin-enriched colostrum preparation.

In a second aspect, the present invention provides a method of prophylaxis, treatment and/or alleviation of fibrosis in a subject, comprising the step of administering to the subject a therapeutically effective amount of a composition that inhibits macrophage infiltration into the tissue, wherein the composition comprises an anti-LPS immunoglobulin-enriched colostrum preparation. In one embodiment macrophage infiltration into the tissue is inhibited by at least 30%. In another embodiment the tissue is selected from the group consisting of lung, liver and heart.

In an alternative and preferred embodiment of this aspect of the invention, the invention provides a method of prophylaxis, treatment or alleviation of liver fibrosis, lung fibrosis and heart fibrosis.

In a further alternative the immunoglobulin preparation is derived from bovine colostrum or from avian eggs.

In a further alternative the anti-LPS immunoglobulin preparation is administered at a dose of about 100 mg to about 2000 mg per day In a second aspect, the invention provides a prophylactic or therapeutic composition for use in any one of the methods described above.

In an alternative and preferred embodiment of the first aspect, the invention provides a therapeutic composition formulated for oral administration.

In a third aspect, the invention provides a method of diagnosis of a fibrotic condition, in which the condition is characterised by pathological fibrosis, comprising the step of assaying a sample of a biological fluid from a subject suspected of suffering from the condition for enzyme ALT or enzyme ALS levels.

A person of ordinary skill in the art will recognise that the biological fluid is selected from the group consisting of blood, plasma, serum, cerebrospinal fluid, urine, and saliva.

In a third aspect, the invention provides a method of prophylaxis, treatment and/or alleviation of organ necrosis, portal inflammation and/or periportal necroinflammation in a subject, comprising the step of administering to the subject a therapeutically effective amount of a composition comprising an anti-LPS immunoglobulin-enriched colostrum preparation.

In different embodiments of the third aspect, the invention provides a method of prophylaxis, treatment and/or alleviation of portal inflammation, periportal necroinflammatory, bridging and confluent necrosis, focal (Spotty) lobular necrosis, hepatocellular apoptosis, alteration of macrophages and/or alterations in F4/80 positive cells.

In a further alternative to this third aspect the immunoglobulin preparation is derived from bovine colostrum or from avian eggs.

In a further alternative to this third aspect the anti-LPS immunoglobulin preparation is administered at a dose of about 100 mg to about 2000 mg per day In a further alternative to this third aspect the invention provides a prophylactic or therapeutic composition for use in any one of the methods described above.

In an alternative and preferred embodiment of the third aspect, the invention provides a therapeutic composition formulated for oral administration.

In a fourth aspect, the invention provides a method of diagnosis of organ necrosis, periportal necroinflammation and/or portal inflammation, comprising the step of assaying a sample of a biological fluid from a subject suspected of suffering from the condition for enzyme ALT or enzyme ALS levels.

In an alternative and preferred embodiment of the fourth aspect, the the biological fluid is selected from the group consisting of blood, plasma, serum, cerebrospinal fluid, urine, and saliva.

DETAILED DESCRIPTION OF THE INVENTION

Figure 1A:
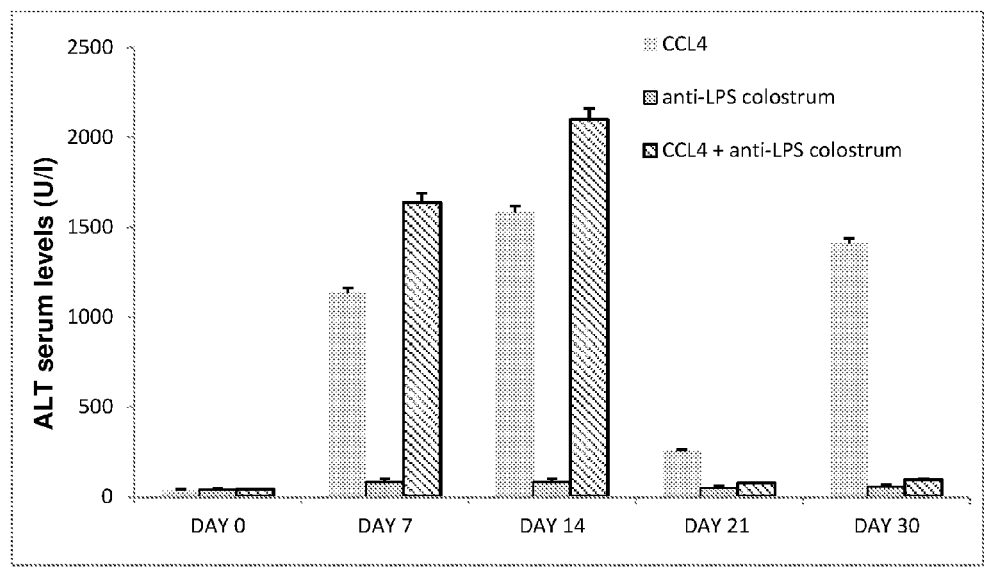
FIG. 1a shows administration of a composition comprising an anti-LPS immunoglobulin-enriched colostrum preparation results in a significant decrease in ALT levels. Levels of the enzyme ALT in mice serum, with measurements starting from day 14 from the start of the assay are shown. Levels of ALT are on the Y axis and days of treatment on the X axis. A significant decrease in ALT levels is shown on days 21 and 30 for the treated group.

The present inventors have shown that treatment of mice with a composition of the present invention inhibits macrophage infiltration into fibrotic tissue. The present inventors have also shown oral administration of a composition comprising an anti-LPS immunoglobulin-enriched colostrum to mice undergoing treatment with CCl4 to prevent hepatic damage and fibrosis by modulating hepatic F4/80 macrophages.

Accordingly, in a first aspect the present invention provides a method of prophylaxis, treatment or alleviation of fibrosis in a subject, comprising the step of administering to the subject a therapeutically effective amount of a composition comprising an anti-LPS immunoglobulin-enriched colostrum preparation.

Without wishing to be bound by theory, as will be described below, anti-LPS enriched colostrum may block LPS-TLR-4 association in the gut, preventing macrophages infiltration to the liver alleviating the macrophage-mediated liver fibrosis.

The development of hepatic fibrosis and cirrhosis occurs in virtually any type of chronic hepatic injury. In terms of chronic liver injury transforming growth factor-β (TGF-β) has an important role in activating hepatic stellate cells (HSC), the main producers of extracellular matrix in the fibrotic liver and the promotion of a fibrogenic phenotype. Toll-like receptor 4 (TLR4) is a humans protein that is encoded by the TLR4 gene[1][2] and it detects lipopolysaccharide from Gram-negative bacteria. TLR4 is therefore important in the activation of the innate immune system. There is accumulating evidence that TLR4-induced activation and sensibilization of HSC may constitute the molecular link between hepatic inflammation and fibrogenesis.

Lipopolysaccharides (LPS), also known as lipoglycans are found in the outer membrane of Gram-negative bacteria, act as endotoxins and elicit among other pathways, strong immune responses in animals. LPS are elevated in experimental models of hepatic fibrosis and in patients with cirrhosis. It is believed that changes in intestinal motility, subsequent alterations of the intestinal microbiota, decreased mucosal integrity, and suppressed immunity in hepatic fibrosis contribute to a failure of the intestinal mucosal barrier, and causes increases in bacterial translocation and LPS levels in later stages of hepatic fibrosis and cirrhosis.

Several studies have demonstrated that modulation of the intestinal microbiota in advanced cirrhosis by probiotics or antibiotics is beneficial for the prevention of bacterial translocation and spontaneous bacterial peritonitis. It has been shown in animal models that antibiotics prevent hepatic injury and fibrosis induced by CCL4 treatment or cholinedeficient diet, and that LPS enhances hepatic fibrosis induced by a MCCD. Treatment of mice with nonabsorbable broad-spectrum antibiotics also resulted in a clear reduction in the fibrotic response of mice, upon bile duct ligation.

The present inventors have shown that treatment of mice with a composition of the present invention inhibits macrophage infiltration into tissue. As phagocytes macrophages are important in the innate as well as the adaptive immune system. In addition, macrophages also play a central role in tissue homeostasis, eliminating dying cells and nursing hemopoietic precursor cells (1). Many of their important functions are performed by cell-surface proteins, such as the complement receptors, the mannose receptor, and scavenger receptors (2, 3). The F4/80 glycoprotein, identified more than 20 years ago as the antigen for the F4/80 mAb, has been established as one of the most specific cell-surface markers for murine macrophages (4, 5). F4/80 is highly and constitutively expressed on most resident tissue macrophages, including the red pulp macrophages in the spleen, microglia in the brain, Kupffer's cells in the liver, and Langerhans' cells in the skin (6). Furthermore, the expression of F4/80 is tightly regulated according to the physiological status of cells. Hepatic fibrosis development requires the coordinated actions of several cell type including Kupffer cells.

Accordingly, in a second aspect the present invention provides a method of prophylaxis, treatment or alleviation of fibrosis or inflammation of a tissue in a subject, comprising the step of administering to the subject a therapeutically effective amount of a composition that inhibits macrophage infiltration into the tissue.

"Treatment" as used herein refers to the reduction or elimination of the severity of a symptom of the disease, the frequency with which such a symptom is exhibited, or both.

"Prophylaxis" as used herein refers to completely or partially preventing or inhibiting a symptom of the disease or the frequency with which such a symptom is exhibited.

"Alleviation" as used herein includes is decrease, suppress, attenuate, diminish, arrest, or stabilize the development or progression of a disease.

"Fibrosis" as used herein refers to, but is not limited to, subjects afflicted with fibrosis of an internal organ, such as fibrosis of internal organs (e.g., liver, lung, kidney, heart, heart blood vessels, gastrointestinal tract, muscles, pancreas, bowel, spleen) which occurs in disorders including pulmonary fibrosis, myelofibrosis, liver cirrhosis, mesangial proliferative glomerulonephritis, crescentic glomerulonephritis, diabetic nephropathy, renal interstitial fibrosis, renal fibrosis in patients receiving cyclosporin, and HIV associated nephropathy.

In a preferred embodiment of this aspect of the invention, the invention provides a method of prophylaxis, treatment or alleviation of liver fibrosis. The composition of the invention comprises as active ingredient a mammalian anti-lipopolysaccharide (anti-LPS) enriched colostrum-derived immunoglobulin preparation.

The immunoglobulin preparation or any fractions thereof, recognizes and binds LPS and any fragments thereof. In one embodiment, the immunoglobulin preparation is derived from bovine colostrum or avian eggs.

Bovine colostrum (BC) is the milk of lactating mammals that is secreted during the first 72 hours following birth. BC differs from regular milk and contains abundant bioactive components—including growth factors, immunoglobulins, lactoperoxidase, lysozyme, lactoferrin, nucleosides, vitamins, peptides, and oligosaccharides—that are of increasing relevance to human health.

It should be further noted that the anti-LPS enriched colostrum-derived immunoglobulin preparations of the invention may be combined with any other immune modulatory drug, including but not limited to other colostrums derived antibodies, other antigen, other adjuvant, other cytokines or any type of molecule that can alter any component of the immune system. The combination can be administered as one product, or in two or more separate products. The combination may be administered together or separately from one another.

According to one specific embodiment, the colostrum-derived anti-LPS enriched immunoglobulin preparation or anti-LPS immunoglobulin preparation may comprise monomeric, dimeric or multimeric immunoglobulin selected from the group consisting of IgG, IgA and IgM and any fragments thereof. In ruminants, the principal compositional difference between colostrum and mature milk is the very high content of colostral immunoglobulin, of which IgG class makes up 80-90%.

Thus, according to a specific embodiment, the colostrum-derived anti-LPS enriched immunoglobulin preparation or anti-LPS immunoglobulin preparation of the invention mainly comprises IgG, specifically, IgG1 and IgG2.

Immunoglobulin G (IgG) as used herein, is a multimeric immunoglobulin, built of two heavy chains and two light chains. Each complex has two antigen binding sites. This is the most abundant immunoglobulin and is approximately equally distributed in blood and in tissue liquids, constituting 75% of serum immunoglobulins in humans. In general, the number of IgG subclasses varied widely between different species, ranging from one subclass in rabbits to seven subclasses in horses, making it difficult to find orthologues. In humans, for example, IgG1 and IgG3 are the most pro-inflammatory IgG subclasses. In mice, however, IgG2a and IgG2b are the most pro-inflammatory IgG molecules showing a greater activity than mouse IgG1 and IgG3 in many in vivo model systems.

Optionally or additionally, the anti-LPS enriched immunoglobulin preparation or anti-LPS immunoglobulin preparation may comprise a secretory antibody, specifically, sIgA.

Dimeric and multimeric IgA and IgM are secreted by a number of exocrine tissues. IgA is the predominant secretory immunoglobulin present in colostrum, saliva, tears, bronchial secretions, nasal mucosa, prostatic fluid, vaginal secretions, and mucous secretions from the small intestine. IgA output exceeds that of all other immunoglobulins, making it the major antibody produced by the body daily and is the major immunoglobulin found in human milk, whey and colostrum. IgM secretion is less abundant but can increase to compensate for deficiencies in IgA secretion. J chain containing IgA is produced and secreted by plasma B immunocytes located in the lamina propria just beneath the basement membrane of exocrine cells. IgA has a typical immunoglobulin four-chain structure ($M_r$ 160,000) made up of two heavy chains ($M_r$ 55,000) and two light chains ($M_r$ 23,000). In humans, there are two subclasses of IgA. These are IgA1 and IgA2 that have one and two heavy chains, respectively. IgA can occur as monomers, dimers, trimers or multimers. In plasma, 10% of the total IgA is polymeric while the remaining 90% is monomeric. The secreted IgA binds to a $M_r$ 100,000 poly-Ig receptor positioned in the basolateral surface of most mucosal cells. The receptor-IgA complex is next translocated to the apical surface where IgA is secreted. The binding of dimeric IgA to the poly-Ig receptor is completely dependent upon the presence of a J chain. Monomeric IgA will not bind to the receptor.

The difference in function of IgG and IgA, follows the position where the molecules operate. IgA is found mainly on mucosal surfaces where there is little in the way of tissue fluid to carry immune cells and chemicals. Therefore, IgA (often as a dimer) would be preferably used for physical neutralisation of pathogens, and may be too effective at other immune functions. IgGs are present in the tissue fluid and blood where there is the full collection of leukocytes, complement system, macrophages etc. may physically neutralize a pathogen effectively and are also more effective in a communication/presentation role than IgA, i.e., they tend to induce better opsonisation by phagocytes (e.g., Killer T cells and macrophages) and switch on the complement system better.

More specifically, the anti-LPS enriched immunoglobulin preparations or anti-LPS immunoglobulin preparations of the invention may be obtained from any one of colostrum, colostrum serum, hyperimmunised milk or colostrum, colostrum whey (either cheese or casein), cheese or casein whey, directly from skim milk, whole milk, or a reconstituted form of such streams.

It should be appreciated that the anti-LPS enriched immunoglobulin preparation or anti-LPS immunoglobulin preparation comprised within the composition of the invention may be any fraction of colostrum. Thus, the term colostrum where used herein includes colostral milk, processed colostral-milk such as colostral milk processed to partly or completely removes one or more of fat, cellular debris, lactose and casein.

The colostrum, or milk, containing the anti-LPS antibodies and optionally, the antigen-specific antibodies may be preferably collected by milking the animal colostrum or milk thus collected can either be used directly, may be further processed, for instance to purify anti-LPS and optionally, antigen-specific antibodies. Methods for the (partial) purification of (LPS and optionally, antigen-specific) antibodies from colostrum or milk are present in the art.

It should be further appreciated that any adjuvants may be added to the compositions of the invention. Appropriate adjuvants therefore may be any antigen, antibody, glycosphingolipids, proteins, cytokines, adhesion molecules, and component that can activate or alter the function of antigen presenting cell or of any other cell related to the immune system in a direct and indirect manner.

Alternatively, the anti-LPS enriched immunoglobulin preparation or anti-LPS immunoglobulin preparation may be an affinity purified antibody or any fragment thereof. The term "antibody" is meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody. It will be appreciated that Fab and F(ab')$_2$ and other fragments of the antibodies useful in the present invention may be used for immuno-modulation, according to the methods disclosed herein for intact antibody molecules. Such fragments are typically produced by proteolytic cleavage, using enzymes such as papain (to produce Fab fragments) or pepsin (to produce F(ab')$_2$ fragments).

An antibody is said to be "capable of specifically recognizing" a certain antigen if it is capable of specifically reacting with an antigen which is in this particular example an antigen or a mixture of antigens specific for a certain immune-related disorder, to thereby bind the molecule to the antibody.

An "antigen" is a molecule or a portion of a molecule capable of being bound by an antibody, which is additionally capable of inducing an animal to produce antibody capable of binding to an epitope of that antigen. An antigen may have one or more than one epitope. The term "epitope" is meant to refer to that portion of any molecule capable of being bound by an antibody that can also be recognized by that antibody. Epitopes or "antigenic determinants" usually consist of chemically active surface groupings of molecules such as amino acids or sugar side chains, and have specific three-dimensional structural characteristics as well as specific charge characteristics.

In yet another embodiment, the anti-LPS enriched immunoglobulin preparation or anti-LPS immunoglobulin preparation used as an active ingredient for the composition of the invention may be obtained from a mammal immunized with LPS or any fragments thereof. Optionally, in addition to LPS, said mammal according to certain embodiments may be further immunized with at least one antigen or a mixture of at least two antigens specific for said disorder, as well as with a mixture of at least two different antibodies directed against at least two different antigens associated with the disease.

According to one embodiment, the LPS or any antigen used for immunizing said mammal, preferably, bovine or avian, may be provided as any one of an isolated and purified peptide, a purified recombinant protein, a fusion protein, cell lysate, membranal preparation, nuclear preparation, or cytosolic preparation of any one of tissue culture cells, primary cells or tissue samples obtained from a subject suffering from said disorder.

In some embodiments of the composition, the composition comprises a constituent of a bird's egg, wherein the bird's egg comprises IgY specific for LPS or a fragment thereof. Crude egg yolk may be used as an antibody source However, avian antibodies are usually purified or concentrated from the yolk prior to use. The constituent of the bird's egg may be concentrated or purified as necessary, as is understood by those skilled in the art In some embodiments of the composition, the composition comprises the yolk of the egg, or any IgY antibody-containing fraction thereof. The yolk is preferable to the white of the egg, as the yolk typically contains much higher concentrations of IgY than does the white. However, the white may contain concentrations of IgY sufficient for some applications.

In one embodiment, the composition of the invention is capable of reducing, eliminating or inhibiting mucosal microbial translocation, thereby modulating immune activation and macrophage inflammation into tissues. Thus, according to certain embodiments, the compositions of the invention may reduce liver damage, reduce or change the number of bacteria or of bacteria related products not related to alteration of the immune system.

According to one embodiment, the invention provides a composition comprising as an active ingredient a mammalian anti-lipopolysaccharide (LPS) enriched colostrum-derived immunoglobulin preparation. Such composition wherein said composition is particularly applicable for the treatment, prevention and prophylaxis of acute or chronic liver disease, cirrhosis and any disease or complication associated therewith, optionally said composition further comprises an additional therapeutic agent or any carrier and adjuvant.

The composition may be formulated for administration orally, by inhalation as an aerosol, or by parenteral, intravaginal, intranasal, mucosal, sublingual, topical, or rectal administration, or any combination thereof.

In one embodiment, the immunoglobulin preparation or any fractions thereof recognizes and binds LPS or any fragments thereof.

In another embodiment, the composition inhibits microbial translocation. In another embodiment, the composition inhibits microbial translocation and thereby modulates immune activation.

In another aspect, the present invention provides a composition comprising a mammalian anti-LPS enriched colostrum-derived immunoglobulin preparation for modulating immune tolerance in a subject, or in another aspect, for modulating oral tolerance in a subject.

According to one preferred embodiment, any of the compositions of the invention may be administered orally or by inhalation as an aerosol or by intravenous, intramuscular, subcutaneous, intraperitoneal, parenteral, transdermal, intravaginal, intranasal, mucosal, sublingual, topical, rectal or subcutaneous administration, or any combination thereof. Orally administered antibodies would be expected to be degraded in the gastrointestinal tract, given the low gastric pH and the presence of gastric and intestinal proteases. However, bovine colostral IgG (BCIg) has been cited as particularly resistant to GI destruction, relative to other immunoglobulins. Early studies of BCIg cited remarkable "resistance to proteolytic digestion in the intestine of a heterologous host". There is also evidence that bovine IgG1 is somewhat more resistant to proteolysis by trypsin, chymotrypsin and pepsin than other Igs. These results drove much of the early development of oral antibody therapy. More specifically, the composition of the invention may be suitable for mucosal administration, for example, pulmonary, buccal, nasal, intranasal, sublingual, rectal, vaginal administration and any combination thereof.

As indicated above, although oral and nasal administration are preferred, it should be appreciated that any other route of administration may be applicable, for example, intravenous, intravenous, intramuscular, subcutaneous, intraperitoneal, parenteral, intravaginal, intranasal, mucosal, sublingual, topical, rectal or subcutaneous administration, or any combination thereof.

Moreover, the anti-LPS enriched immunoglobulin preparation used by the compositions and combined compositions of the invention may be prepared in preparations such as food additives, aqueous solutions, oily preparations, emulsions, gels, etc., and these preparations may be administered orally, topically, rectally, nasally, bucally, or vaginally. The preparations may be administered in dosage formulations containing conventional non-toxic acceptable carriers and may also include one or more acceptable additives, including acceptable salts, polymers, solvents, buffers, excipients, bulking agents, diluents, excipients, suspending agents, lubricating agents, adjuvants, vehicles, deliver systems, emulsifiers, dis-integrants, absorbents, preservatives, surfactants, colorants, flavorants or sweeteners. An optional dosage form of the present invention may be a powder for incorporation into beverages, pills, syrup, capsules, tablets, granules, beads, chewable lozenges or food additives, using techniques known in the art. Thus, immuno-modulating composition of the invention may be administered in a form selected from the group consisting of orally-active powders, pills, capsules, teas, extracts, dried extracts, subliguals, sprays, dispersions, solutions, suspensions, emulsions, foams, syrups, lotions, ointments, gels, pastes, dermal patches, injectables, vaginal creams and suppositories.

Therapeutic formulations may be administered in any conventional dosage formulation. Formulations typically comprise at least one active ingredient, as defined above, together with one or more acceptable carriers thereof.

Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal or by inhalation) administration. The formulations may conveniently be presented in unit dosage form and may be prepared by any methods well known in the art of pharmacy. The nature, availability and sources, and the administration of all such compounds including the effective amounts necessary to produce desirable effects in a subject are well known in the art and need not be further described herein.

The preparation of pharmaceutical compositions is well known in the art and has been described in many articles and textbooks, see e.g., Remington's Pharmaceutical Sciences, Gennaro A. R. ed., Mack Publishing Co., Easton, Pa., 1990, and especially pp. 1521-1712 therein, fully incorporated herein by reference.

The pharmaceutical composition of the invention can be administered and dosed in accordance with good medical practice.

The composition of the invention may comprise the active substance in free form and be administered directly to the subject to be treated. Formulations typically comprise at least one active ingredient, as defined above, together with one or more acceptable carriers thereof. Each carrier should be both pharmaceutically and physiologically acceptable in the sense of being compatible with the other ingredients and not injurious to the patient.

Formulations include those suitable for oral, nasal, or parenteral (including subcutaneous (s.c.), intramuscular (i.m.), intraperitoneal (i.p.), intravenous (i.v.) and intradermal or by inhalation to the lung mucosa) administration. The formulations may conveniently be presented in unit dosage form and may be prepared by any methods well known in the art of pharmacy. The nature, availability and sources, and the administration of all such compounds including the effective amounts necessary to produce desirable effects in a subject are well known in the art and need not be further described herein.

The pharmaceutical compositions of the invention generally comprise a buffering agent, an agent that adjusts the osmolarity thereof, and optionally, one or more pharmaceutically acceptable carriers, excipients and/or additives as known in the art. Supplementary active ingredients can also be incorporated into the compositions. The carrier can be solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

As used herein "pharmaceutically acceptable carrier" includes any and all solvents, dispersion media, coatings, antibacterial and antifungal agents and the like. The use of such media and agents for pharmaceutical active substances is well known in the art. Except as any conventional media or agent is incompatible with the active ingredient, its use in the therapeutic composition is contemplated.

In instances in which oral administration is in the form of a tablet or capsule, the active drug components (anti-LPS enriched immunoglobulin preparation) can be combined with a non-toxic pharmaceutically acceptable inert carrier such as lactose, starch, sucrose, glucose, modified sugars, modified starches, methylcellulose and its derivatives, dicalcium phosphate, calcium sulfate, mannitol, sorbitol, and other reducing and non-reducing sugars, magnesium stearate, stearic acid, sodium stearyl fumarate, glyceryl behenate, calcium stearate and the like. For oral administration in liquid form, the active drug components can be combined with non-toxic pharmaceutically acceptable inert carriers such as ethanol, glycerol, water and the like. When desired or required, suitable binders, lubricants, disintegrating agents and coloring and flavoring agents can also be incorporated into the mixture. Stabilizing agents such as antioxidants, propyl gallate, sodium ascorbate, citric acid, calcium metabisulphite, hydroquinone, and 7-hydroxycoumarin can also be added to stabilize the dosage forms. Other suitable compounds can include gelatin, sweeteners, natural and synthetic gums such as acacia, tragacanth, or alginates, carboxymethylcellulose, polyethylene, glycol, waxes and the like.

As indicated above, it should be noted that the anti-LPS enriched immunoglobulin preparation used by the invention may be obtained from a mammal, immunized with LPS or any fragments thereof and optionally, in addition, with at least one antigen or a mixture of at least two antigens specific for the disorder to be treated. Means and methods of the invention are suited to obtain high and prolonged antigen-specific antibody production in the colostrum, milk or milk products of any lactating mammal. Preferably, said animal is a farm-animal. Farm animals are animals that are used on a commercial basis by man, be it for the production of milk, meat or even antibodies. Farm-animals already used for the commercial scale production of milk are preferred for the present invention since for these animals special lines and/or breeds exist that are optimized for milk production. Preferably, said farm-animal is a cow or a goat. More preferably said farm-animal is a cow.

As shown, by the Examples, the compositions of the invention significantly decreased the serum levels of ALT and AST. Therefore, according to one embodiment, the pharmaceutical composition of the invention leads to at least one of a decrease in the serum levels of ALT and AST in a subject suffering. Wherein indicated decrease, reduction, inhibition, it is meant that the composition of the invention leads to a reduction of about 5% to 99% of the serum level of any one of ALT or AST, in a subject. More specifically, such reduction may be a reduction of about, 5%, 10%, 15%, 20%, 25%, 30%, 35%, 40%, 45%, 50%, 55%, 60%, 65%, 70%, 75%, 80%, 85%, 90%, 95% and over 99%, as compared to the levels prior to the treatment, or the levels of untreated control. Wherein indicated increase, elevation, enhancement, induction, it is meant that the composition of the invention leads to induction, or increase of about 5% to 99%. More specifically, such increase may be an increase of about, 5%, 10%, 15%, 20%, 25%, 30%, 35%, 40%, 45%, 50%, 55%, 60%, 65%, 70%, 75%, 80%, 85%, 90%, 95% and over 99%, as compared to the levels prior to the treatment, or the levels of untreated control.

Accordingly, a human subject in need of treatment may also be presumptively diagnosed by serum tests of liver enzymes, for example, indicated by elevated serum levels (often moderately elevated, e.g., elevated approximately 2, 3, 4, 5, 6, 7, 9, 10, 11, or 12-fold above normal levels) of liver enzymes (such as, e.g., alanine aminotransferase, aspartate aminotransferase, γ-glutamyltransferase, alkaline phosphatase). For example, alanine aminotransferase (ALT or SGPT) values greater than 32, 24, or 56 units per liter of serum or at least 2, 3, 4, 5, 6, 7, 8, 9, 10, 11, 12, or more times normal values may be indicative of a disorder associated with hepatic lipid deposits, or by aspartate aminotransferase (AST or SGOT) values greater than 40 units per liter of serum or at least 2, 3, 4, 5, 6, 7, 8, 9, 10, 11, 12, or more times normal values.

In addition to being presumptively diagnosed by serum tests of liver enzymes, a subject in need of treatment may also be presumptively diagnosed by noninvasive techniques, such as FIBROSCAN and FIBROTEST.

A subject in need of treatment may be definitively diagnosed by liver biopsy.

The administration of the composition of the present invention in order to practice the present methods of therapy is carried out by administering a therapeutically effective amount of the compounds in the composition to a subject in need of such treatment or prophylaxis. The need for a prophylactic administration according to the methods of the present invention is determined via the use of the well known risk factors as described herein.

Each oral dose form may, for example, comprise the colostrum equivalent of less than 1200 mg (dry weight basis), preferably 800 mg, preferably less than 400 mg, more preferably less than 200 mg. By colostrum equivalent we mean the amount of raw colostrum, howsoever purified, which is processed to provide the contents of a dose form.

For oral administration, the oral dose form may comprise 5 mg to 500 mg bovine colostrum powder (BCP) (dry weight basis), e.g. 5, 10, 15, 20, 25, 30, 35, 40, 45, 50, 55, 60, 70, 80, 90, 100, 125, 150, 175, 200, 225, 250, or 500 mg.

The oral dose form may comprise 500 mg to 5000 mg bovine colostrum powder (dry weight basis), e.g. 500, 750, 1000, 1250, 1500, 1750, 2000, 2250, 2500, 2750, 3000, 3250, 3500, 3750, 4000, 4250, 4500, 4750 or 5000 mg.

Suitable dosage ranges are, e.g. from about 5 mg to about 5000 mg/day, preferably 50 mg to about 5000 mg/day, more preferably 500 mg to about 5000 mg/day, or most preferably 1500 mg to about 2000 mg/day BCP (dry weight basis). In one preferred embodiment, the dose is 1800 mg/day BCP (dry weight basis).

In one embodiment, the anti-LPS immunoglobulin preparation is administered at a dose of about 100 mg to about 2000 mg per day.

In one embodiment the antibodies are present in the composition for oral administration in an amount sufficient to provide from at least 7% by dry weight of the composition of IgG.

In another embodiment the antibodies are present in the composition for oral administration in an amount sufficient to provide from at least 40% by weight of the composition of IgG.

Accordingly, for oral administration, the oral dose form may comprise 2 mg to 200 mg IgG, e.g. 2, 4, 6, 8, 10, 12, 14, 16, 18, 20, 25, 30, 35, 40 45, 50, 55, 60, 65, 70, 75, 80, 85, 90, 95, 100, 110, 125, 150, 175, or 200 mg IgG.

The oral dose form may comprise 200 mg to 2000 mg IgG e.g. 200, 300, 400, 500, 600, 700, 800, 900, 1000, 1100, 1200, 1300, 1400, 1500, 1600, 1700, 1800, 1900 or 2000 mg IgG.

In one embodiment antibodies specific to the antigen are present in the composition for oral administration in an amount sufficient to provide from at least 10% specific IgG of the weight of IgG.

Accordingly, for oral administration, the oral dose form may comprise 0.2 mg to 20 mg specific IgG, e.g. 0.2, 0.4, 0.6, 0.8, 1, 1.2, 1.4, 1.6, 1.8, 2.0, 2.5, 3.0, 3.5, 4.0, 4.5, 5.0, 5.5, 6.0, 6.5, 7.0, 7.5, 8.0, 8.5, 9.0, 9.5, 10.0, 11.0, 12.5, 15.0, 17.5, or 20.0 mg specific IgG.

Suitable dosage ranges are, e.g. from about 2 to about 200 mg/day, preferably 20 to about 2000 mg/day, more preferably 200 to about 2000 mg/day, or most preferably 600 mg to about 800 mg/day IgG. In one preferred embodiment, the dose is 720 mg/day IgG.

In one embodiment, the anti-LPS immunoglobulin preparation is not administered at a dose of about 600 mg per day (dry weight volume).

The oral dose form may be administered for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 days.

In one embodiment, the oral dose form is administered for 30 days.

In one embodiment, the anti-LPS immunoglobulin preparation is administered for 30 days at dose of 1.8 g/day. In one embodiment, the anti-insulin immunoglobulin preparation is administered for 30 days at dose of 1.2 g/day.

The oral dose form preferably comprises colostrum derived from the hyperimmune colostrum and/or colostrum which has been added to the polyclonal antibodies in accordance with the teaching of PCT/AU03/00348 (Pub. No.: WO/2003/080082). The oral dosage form may also comprise a buffer system such as that disclosed in PCT/AU2005/001746 (Pub. No.: WO/2006/053383). The contents of these patents are incorporated by reference.

The term "therapeutically effective amount" as used herein means the amount of the active compounds in the composition that will elicit the biological or medical response in a tissue, system, subject, or human that is being sought by the researcher, veterinarian, medical doctor or other clinician, which includes alleviation of the symptoms of the disorder being treated. The novel methods of treatment of this invention are for disorders known to those skilled in the art.

The term "prophylactically effective amount" as used herein means the amount of the active compounds in the composition that will elicit the biological or medical response in a tissue, system, subject, or human that is being sought by the researcher, veterinarian, medical doctor or other clinician, to prevent the onset of the symptoms of the disorder in a subject at risk of developing the disorder.

The magnitude of prophylactic or therapeutic dose of the active ingredients can, of course, vary with the nature of the severity of the condition to be treated. It can also vary according to the age, weight and response of the individual patient, and may be administered in subject in single or divided doses. On the other hand, it may be necessary to use dosages outside the ranges provided herein in some cases.

The anti-LPS immunoglobulin preparation may be administered at a dose of about 5 mg to about 25000 mg per day, 10 mg to about 20000 mg per day, 25 mg to about 15000 mg per day, 100 mg to about 2000 mg per day, or about 1800 mg per day or about 1200 mg per day. In one embodiment, the anti-LPS immunoglobulin preparation is not administered at a dose of about 600 mg per day.

The anti-LPS immunoglobulin preparation may be formulated for administration at a dose of about 5 mg to about 25000 mg per day, about 10 mg to about 20000 mg per day, about 25 mg to about 15000 mg per day, about 100 mg to about 2000 mg per day or about 1800 mg per day or about 1200 mg per day.

In one embodiment, the anti-LPS immunoglobulin preparation is not formulated for administration at a dose of about 600 mg per day.

It is preferred the bacteria from which each type of O antigen is isolated are grown in separate bacterial culture systems, and after separation of the O antigen from the bacteria, the component antigens are added together to form a component of the vaccine.

Methods of preparing LPS/O antigen are known in the art and described in WO/2004/078209, which is incorporated herein by reference. Methods of preparing hyperimmune bovine colostrum (HIBC) are also described in WO/2004/078209.

The anti-LPS immunoglobulin preparation may be prepared by immunizing a mammal or avian with LPS from multiple E. coli strains. The mammal or avian may be immunized with LPS selected from the group consisting of O6, O8, O15, O25, O27, O63, O78, O114, O115, O128, O148, O153, O159, and other LPS associated with enterotoxigenic E. coli.

The mammal or avian may be immunized with LPS selected from the group consisting of O78, O6, O8, O129 and O153 LPS. The LPS may comprise O78 LPS.

In an alternative and preferred embodiment of the first aspect, the invention provides a method of prophylaxis, treatment or alleviation of lung fibrosis.

In a further alternative and preferred embodiment of the second aspect, the invention provides a method of prophylaxis, treatment or alleviation of heart fibrosis.

In a further alternative the immunoglobulin preparation is derived from bovine colostrum or from avian eggs.

In a further alternative the anti-LPS immunoglobulin preparation is administered at a dose of about 100 mg to about 2000 mg per day In a second aspect, the invention provides a prophylactic or therapeutic composition for use in any one of the methods described above.

In an alternative and preferred embodiment of the first aspect, the invention provides a therapeutic composition formulated for oral administration.

In a third aspect, the invention provides a method of diagnosis of a fibrotic condition, in which the condition is characterised by pathological fibrosis, comprising the step of assaying a sample of a biological fluid from a subject suspected of suffering from the condition for enzyme ALT or enzyme ALS levels.

A person of ordinary skill in the art will recognise that the biological fluid is selected from the group consisting of blood, plasma, serum, cerebrospinal fluid, urine, and saliva.

In a third aspect, the invention provides a method of prophylaxis, treatment and/or alleviation of organ necrosis, portal inflammation or periportal necroinflammation in a subject, comprising the step of administering to the subject a therapeutically effective amount of a composition comprising an anti-LPS immunoglobulin-enriched colostrum preparation.

In different embodiments of the third aspect, the invention provides a method of prophylaxis, treatment and/or alleviation of portal inflammation, periportal necroinflammatory, bridging and confluent necrosis, focal (Spotty) lobular necrosis, hepatocellular apoptosis, alteration of macrophages and/or alterations in F4/80 positive cells.

In a further alternative to this third aspect the immunoglobulin preparation is derived from bovine colostrum or from avian eggs.

In a further alternative to this third aspect the anti-LPS immunoglobulin preparation is administered at a dose of about 100 mg to about 2000 mg per day In a further alternative to this third aspect the invention provides a prophylactic or therapeutic composition for use in any one of the methods described above.

In an alternative and preferred embodiment of the third aspect, the invention provides a therapeutic composition formulated for oral administration.

In a fourth aspect, the invention provides a method of diagnosis of organ necrosis, periportal necroinflammation and/or portal inflammation, comprising the step of assaying a sample of a biological fluid from a subject suspected of suffering from the condition for enzyme ALT or enzyme ALS levels.

In an alternative and preferred embodiment of the fourth aspect, the the biological fluid is selected from the group consisting of blood, plasma, serum, cerebrospinal fluid, urine, and saliva.

It will be noted by the skilled addressee that one may test the effect of this compound in models of lung fibrosis such as bleomycin fibrosis, as well as in other organs.

Abbreviations used herein are as follows:
ALT Alanine aminotransferase
AST Aspartate aminotransferase
BC Bovine colostrum
CCl4 Carbon tetrachloride
FCS Fetal Calf Serum
HSC hepatic stellate cells
IPF Idiopathic pulmonary fibrosis
LPS Lipopolysaccharides
TGF-β injury transforming growth factor-β
TLR4 Toll-like receptor 4

The invention will now be described in detail by way of reference only to the following non-limiting examples and drawings.

EXAMPLES

Example 1: Materials and Methods

Mice

Male C57BL/6 mice (9-10 weeks old) were purchased from Harlan Laboratories (Jerusalem, Israel). All mice were maintained in specific pathogen-free conditions. Mice were maintained in the Animal Core of the Hadassah-Hebrew University Medical School. All mice were administered standard laboratory chow and water ad libitum and kept in a 12-hour light/dark cycle.

Fibrosis Model

Carbon tetrachloride (CCL4, Sigma-Aldrich, Rehovot, Israel) was used to induce hepatic fibrosis. CCL4 was diluted 1:10 with sunflower oil and 200 μl were administered intraperitoneal (i.p) twice a week for 4 weeks.

Anti-LPS Colostrum

Anti-LPS colostrum powder (Immuron, Australia) was dissolved in sterile DDW for a final concentration of 25 mg/ml. 500 μg anti-LPS colostrum in 20 μl was administered orally to the mice every day, starting the first day of CCL4 treatment. Four control mice received 20 μl of sterile water. The composition comprising an anti-LPS immunoglobulin-enriched colostrum preparation used herein ("Anti-LPS colostrum") is described in PCT/AU2004/000277, which is incorporated herein by reference.

Experimental Design

| Group | CCL4 | Anti-LPS colostrum |
|---|---|---|
| A | + | — |
| B | + | 500 μg/mouse |
| C | − | 500 μg/mouse |

Measurements

Alanine aminotransferase (ALT) and aspartate aminotransferase (AST) serum levels (U/I) and mice body weight was measured every week. ALT and AST were measured using Reflotron sticks (Roche Pharmaceuticals, Israel) with a Reflotron reader. On sacrifice spleen and liver weight was measured and their weight ratio was calculated.

Pathology

Fibrosis scoring was evaluated by the following pathology tests: Metavir fibrosis score was scaled 0-4 as following: 0=no fibrosis, 1=Stellate enlargement of portal tracts without septae formation, 2=Enlargement of portal tracts with rare septae formation, 3=Numerous septae with fibrosis, 4=cirrhosis; periportal necroinflammatory changes was scaled 0-3 as following: 0=absent, 1=moderate alteration of the periportal tract in some portal tracts or focal, 2=Diffuse alteration of the periportal tract in some portal tracts or focal, 3=Diffuse alteration of the periportal plate in all portal tracts; Bridging and Confluent Necrosis was scaled 0-1 as following: 0=absent, 1=present; portal inflammation was scaled 1-3 as following: 0=absent, 1=presence of mononuclear aggregates in some portal tract, 2=mononuclear aggregates in all portal tracts, 3=Large and dense mononuclear aggregates in all portal tracts.

Immunohistochemical Staining

Liver samples were fixed in 4% neutral-buffered formalin and embedded in paraffin. 5 μM sections were dewaxed and hydrated through graded ethanol dilutions then cooked in citrate buffer (pH 6, 10 mM) in a pressure cooker at 115° C. for 3 min. Endogenous peroxidase activity was blocked with 3% hydrogen peroxide followed by washing. The sections were then incubated overnight with F4/80 antibody (SbD Serotec, Kidlington, UK). Secondary Ab exposure was performed using the Mach 3 Rabbit tool kit (Biocare Medical, CA, USA) following the manufacturers' instructions. All sections were counterstained with hematoxylin and were visualized using an Olympus light microscope. Quantification was performed by visualizing the slides.

Isolation of Intrahepatic Lymphocytes

Livers were removed after sacrifice and stored in RPMI-1640 supplemented with 10% Fetal Calf Serum (FCS). Livers were crushed through a stainless mesh (size 60, Sigma). Ten milliliters of Lymphoprep (Ficoll, Axis-Shield PoC AS, Oslo, Norway) was loaded with a similar volume of the cell suspension in 50-ml tubes. The tubes were centrifuged at 1800 rpm for 18 min. Cells present in the interface were collected and centrifuged again at 1800 rpm for 10 min to obtain a pellet of cells depleted of hepatocytes.

Flow Cytometry for Lymphocyte Subsets

Flow cytometry was performed on $1\times10^6$ hepatic lymphocyte in 100 ul PBS with 1% BSA. Cells were incubated with eFlour450-conjugated F4/80 antibody (eBioscience, San Diego, Calif., USA) at the recommended dilutions or with isotype control antibodies for 30 minutes at 4° C. FACS analyzed using a FACS LSR II instrument (Becton Dickinson, San Jose, Calif.) with FCS express V.3 software (De-Novo software, CA, USA). Only live cells were counted, and background fluorescence from non-antibody-treated lymphocytes was subtracted.

Statistics

Results are presented as mean values±standard deviation. Student's T-test was used for statistical significant correlations.

Figure 3A:
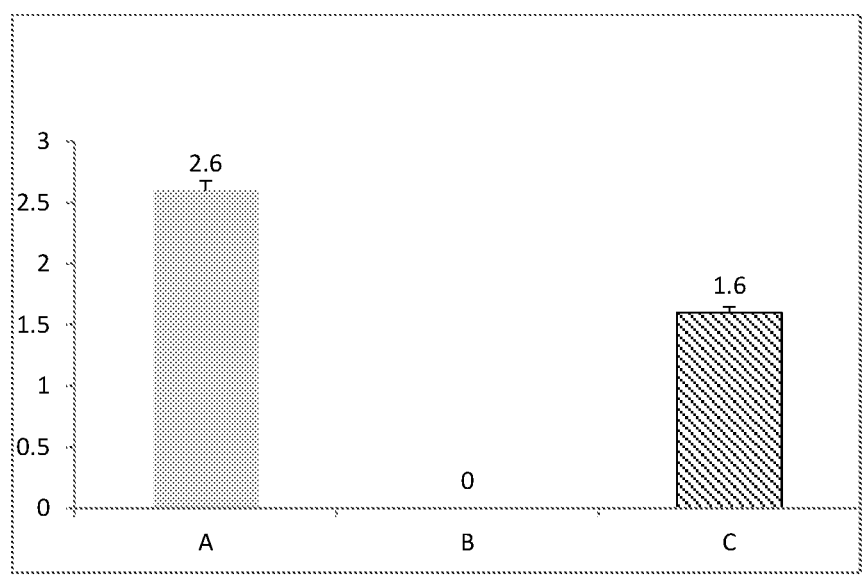
FIG. 3a shows administration of a composition comprising an anti-LPS immunoglobulin-enriched colostrum preparation results in a significant decrease in levels of fibrosis scoring. Levels of fibrosis scoring in periportal necroinflammation changes for each of the mice test samples are shown. The Y axis shows the periportal necroinflammatory score for each of the three groups. A significant decrease in the score is shown for the treated animals.

Example 2: Anti-LPS Colostrum Decreases Bacterial Translocation and Improves Immune Response in CCL4 Induced Fibrosis and the Effect on the Fibrosis State of the Liver FIG. 3a shows administration of a composition comprising an anti-LPS immunoglobulin-enriched colostrum preparation results in a significant decrease in levels of fibrosis scoring. Levels of fibrosis scoring in periportal necroinflammation changes for each of the mice test samples are shown. The Y axis shows the periportal necroinflammatory score for each of the three groups. A significant decrease in the score is shown for the treated animals.

Figure 3B:
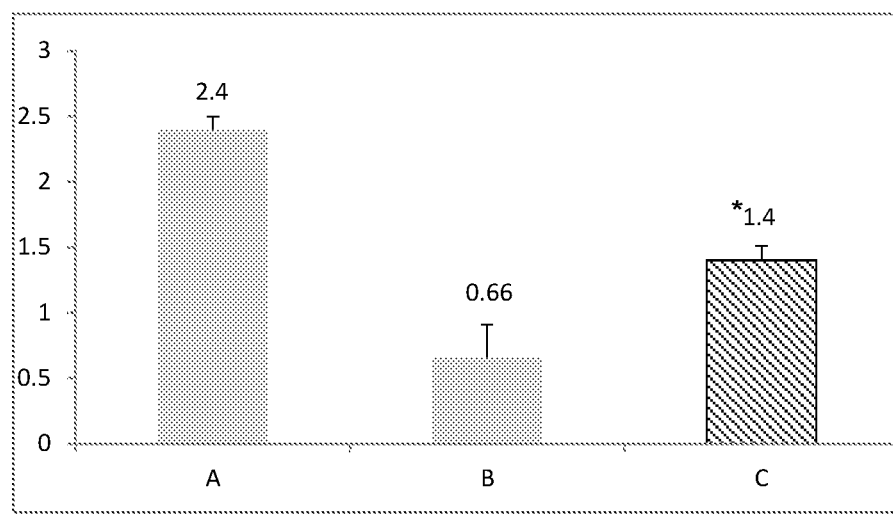
FIG. 3b shows administration of a composition comprising an anti-LPS immunoglobulin-enriched colostrum preparation results in a significant decrease in levels of fibrosis scoring. Levels of fibrosis scoring in portal inflammation changes for each of the mice test samples is shown. The Y axis shows the portal inflammation score for each of the three groups. A significant decrease in the score is shown for the treated animals.

FIG. 3b shows administration of a composition comprising an anti-LPS immunoglobulin-enriched colostrum preparation results in a significant decrease in levels of fibrosis scoring. Levels of fibrosis scoring in portal inflammation changes for each of the mice test samples is shown. The Y axis shows the portal inflammation score for each of the three groups. A significant decrease in the score is shown for the treated animals.

Figure 3C:
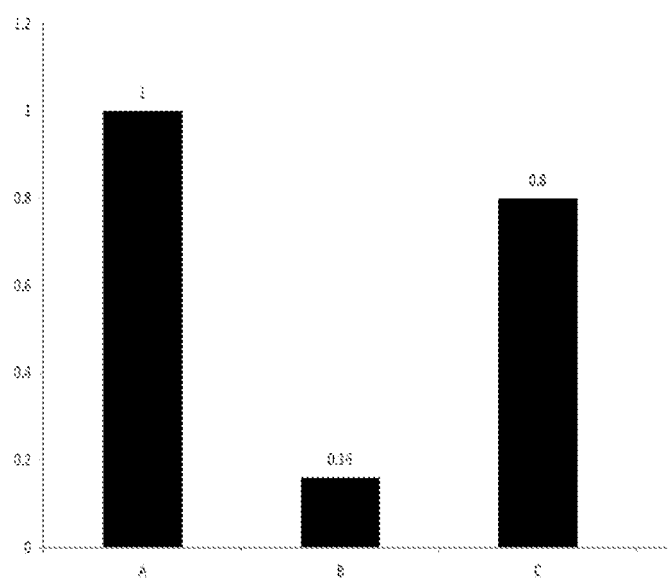
FIG. 3c shows administration of a composition comprising an anti-LPS immunoglobulin-enriched colostrum preparation results in a significant decrease in levels of fibrosis scoring. Levels of fibrosis scoring according to bridging and confluent necrosis in mice livers for each of the test samples are shown. The Y axis shows the bridging and confluent necrosis score for each of the three groups. A significant decrease in the score is shown for the treated animals.

FIG. 3c shows administration of a composition comprising an anti-LPS immunoglobulin-enriched colostrum preparation results in a significant decrease in levels of fibrosis scoring. Levels of fibrosis scoring according to bridging and confluent necrosis in mice livers for each of the test samples are shown. The Y axis shows the bridging and confluent necrosis score for each of the three groups. A significant decrease in the score is shown for the treated animals.

Figure 4:
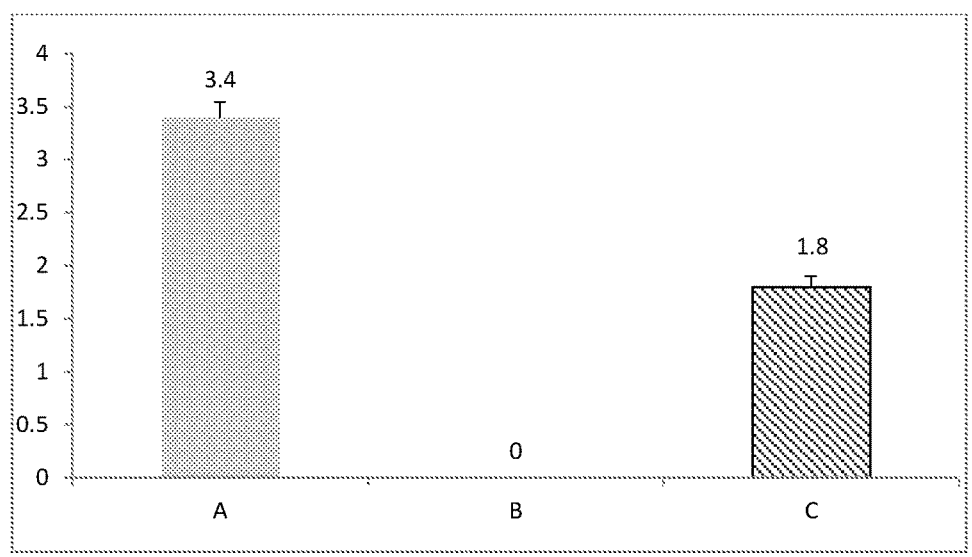
FIG. 4 shows administration of a composition comprising an anti-LPS immunoglobulin-enriched colostrum preparation results in a significant decrease in levels of fibrosis scoring. Levels of fibrosis scoring for each of the mice test samples. The Y axis shows the fibrosis score for each of the three groups. A significant decrease in the score is shown for the treated animals.

FIG. 4 shows administration of a composition comprising an anti-LPS immunoglobulin-enriched colostrum preparation results in a significant decrease in levels of fibrosis scoring. Levels of fibrosis scoring for each of the mice test samples. The Y axis shows the fibrosis score for each of the three groups. A significant decrease in the score is shown for the treated animals.

Figure 5:
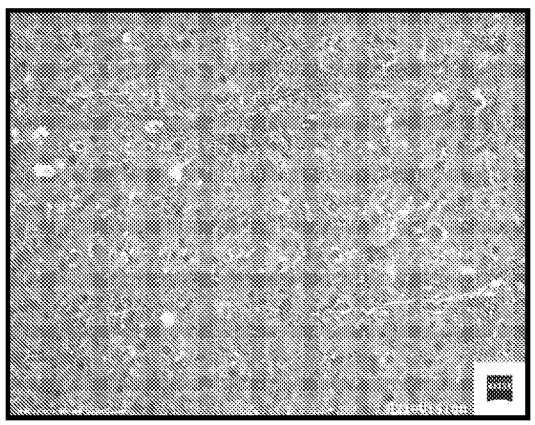
FIG. 5 shows administration of a composition comprising an anti-LPS immunoglobulin-enriched colostrum preparation results in a significant normalisation of liver histopathology. H&E staining of representative liver samples from each of experimental groups showing significant normalization of the liver biopsies in treated animals.
Figure 5:
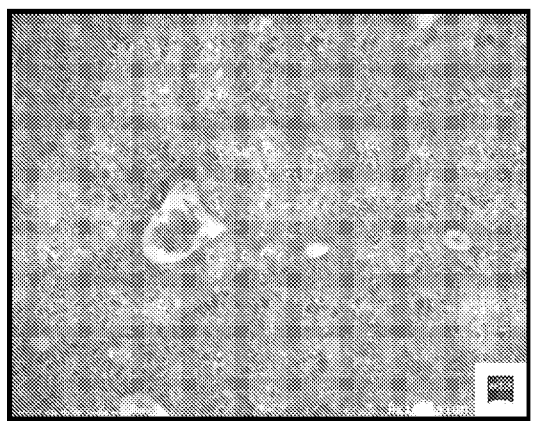
Figure 5:

FIG. 5 shows administration of a composition comprising an anti-LPS immunoglobulin-enriched colostrum preparation results in a significant normalisation of liver histopathology H&E staining of representative liver samples from each of experimental groups showing significant normalization of the liver biopsies in treated animals.

Figure 6:
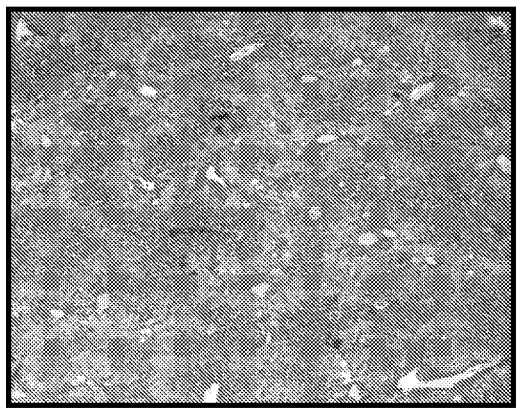
FIG. 6 shows administration of a composition comprising an anti-LPS immunoglobulin-enriched colostrum preparation results in marked attenuation of fibrosis. Trichrome staining of liver samples as a measure of the degree of liver fibrosis is shown. Marked attenuation of the fibrosis is shown in the treated animals
Figure 6:
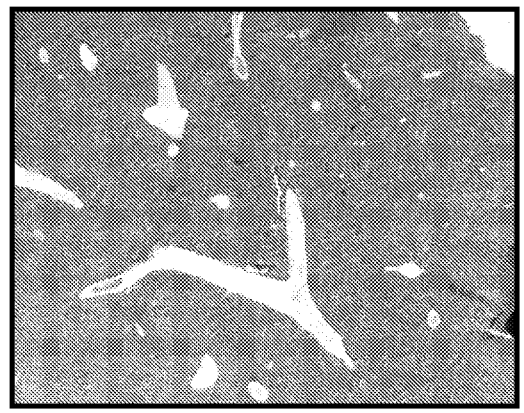
Figure 6:
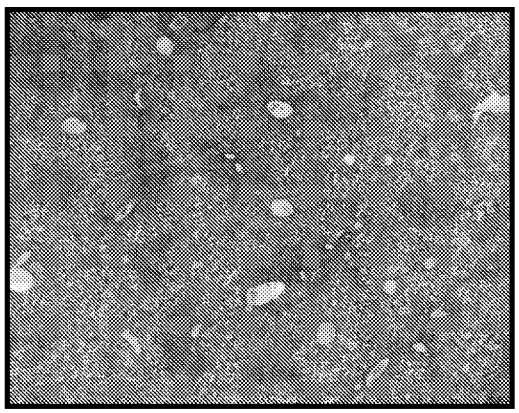
Figure 7A:
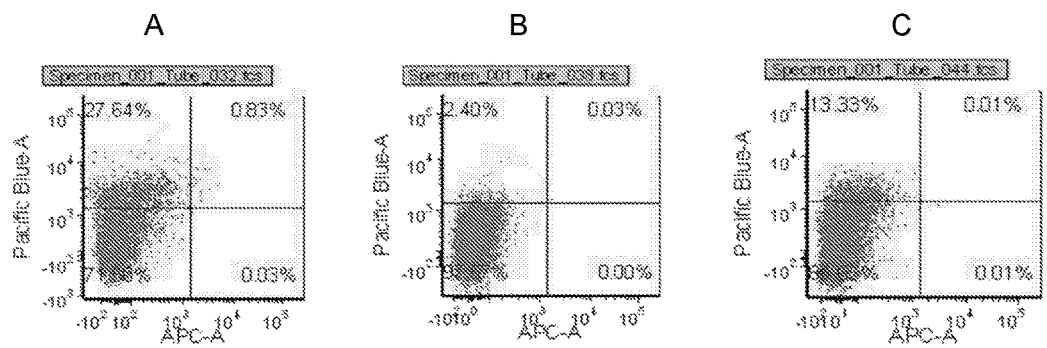
FIG. 7a shows administration of a composition comprising an anti-LPS immunoglobulin-enriched colostrum preparation results in a marked reduction of macrophage infiltration into the liver. Representative FACS sorting samples showing the percentage of F4/80 positive cells in the liver of test samples as measured by FACS analysis is shown.

FIG. 6 shows administration of a composition comprising an anti-LPS immunoglobulin-enriched colostrum preparation results in marked attenuation of fibrosis. Trichrome staining of liver samples as a measure of the degree of liver fibrosis is shown. Marked attenuation of the fibrosis is shown in the treated animals FIG. 7a shows administration of a composition comprising an anti-LPS immunoglobulin-enriched colostrum preparation results in a marked reduction of macrophage infiltration into the liver. Representative FACS sorting samples showing the percentage of F4/80 positive cells in the liver of test samples as measured by FACS analysis is shown.

Figure 7B:
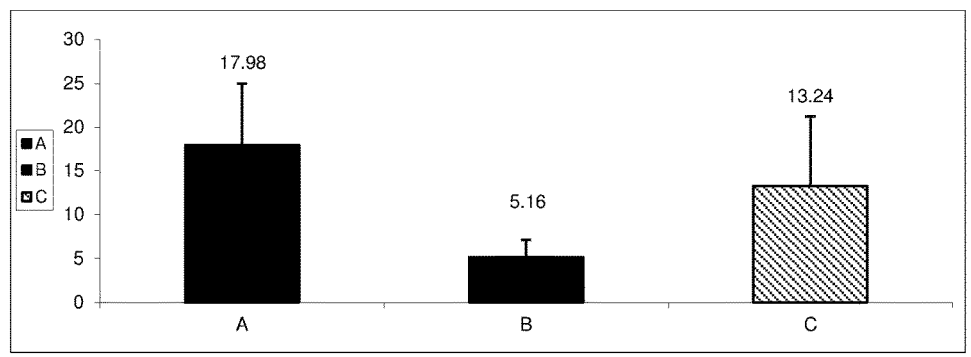
FIG. 7b shows administration of a composition comprising an anti-LPS immunoglobulin-enriched colostrum preparation results in a marked reduction of macrophage infiltration into the liver. The percentage of F4/80 positive cells in the liver of test samples as measured by immunohistochemistry quantification is shown. The Y axis shows percentage of cells for each of the groups. Marked reduction in the number of F4/80 positive cells is shown for the treated animals.

FIG. 7b shows administration of a composition comprising an anti-LPS immunoglobulin-enriched colostrum preparation results in a marked reduction of macrophage infiltration into the liver. The percentage of F4/80 positive cells in the liver of test samples as measured by immunohistochemistry quantification is shown. The Y axis shows percentage of cells for each of the groups. Marked reduction in the number of F4/80 positive cells is shown for the treated animals.

The above discussed methods establish the ability of a composition comprising an anti-LPS immunoglobulin-enriched colostrum preparation to decrease bacterial translocation, improve the mouse immune response in CCl4 induced fibrosis, and reduce fibrosis of the liver.

Effect of Anti-LPS Colostrum on ALT and AST Serum Levels

Daily administration of anti-LPS colostrum reduced liver damage starting from day 14 as measured by ALT (FIG. 1a) and AST (FIG. 1b) levels in mice serum. In both FIGS. 1a and 1b, enzyme levels of ALT and AST in mice serum are shown on the Y axis and days of treatment on the X axis. A significant decrease in ALT and AST levels is shown on days 21 and 30 for the treated group in both figures.

FIG. 1a shows administration of a composition comprising an anti-LPS immunoglobulin-enriched colostrum preparation results in a significant decrease in ALT levels. Levels of the enzyme ALT in mice serum, with measurements starting from day 14 from the start of the assay are shown. Levels of ALT are on the Y axis and days of treatment on the X axis. A significant decrease in ALT levels is shown on days 21 and 30 for the treated group.

Figure 1B:
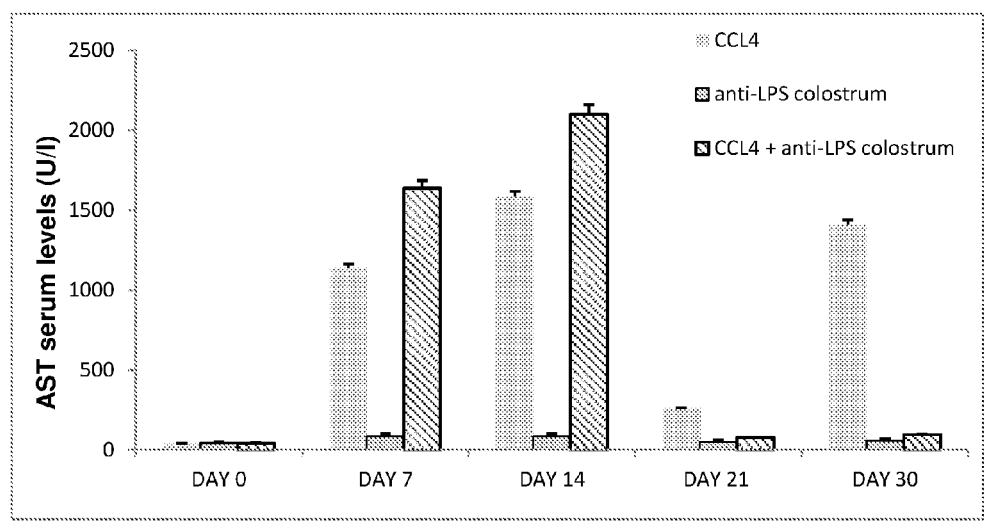
FIG. 1b shows administration of a composition comprising an anti-LPS immunoglobulin-enriched colostrum preparation results in a decrease in ALT level. Levels of the enzyme ALS in mice serum, with measurements starting from day 14 from the start of the assay are shown. Levels of AST are on the Y axis and days of treatment on the X axis. A significant decrease in ALT levels is shown on days 21 and 30 for the treated group.

FIG. 1b shows administration of a composition comprising an anti-LPS immunoglobulin-enriched colostrum preparation results in a decrease in ALT level. Levels of the enzyme ALS in mice serum, with measurements starting from day 14 from the start of the assay are shown. Levels of AST are on the Y axis and days of treatment on the X axis. A significant decrease in ALT levels is shown on days 21 and 30 for the treated group.

ALT and AST are transaminase enzymes, found in plasma and in various bodily tissues. Both enzymes are associated with liver parenchymal cells but ALT is found predominantly in the liver, whereas AST is found in other organs, such as heart, skeletal muscle, kidneys, brain, and red blood cells.

ALT catalyzes the transfer of an amino group from L-alanine to $\alpha$-ketoglutarate, being two parts of the alanine cycle. Significantly elevated levels of ALT can suggest the existence of viral hepatitis, diabetes, congestive heart failure, liver damage, bile duct problems, infectious mononucleosis, or myopathy.

AST catalyzes the reversible transfer of an $\alpha$-amino group between aspartate and glutamate and, as such, is an important enzyme in amino acid metabolism. Elevated levels of both ALT and AST enzymes indicate liver disfunction. Subsequently, the reduction of such levels is also evidence of improvement in liver health and/or the reversal of liver damage.

Example 3: Effect of Anti-LPS Colostrum on and Liver Weight

Advanced fibrosis and cirrhosis cause a decrease in liver volume and an increase in spleen volume. Treatment with anti-LPS colostrum improved these markers.

Figure 2A:
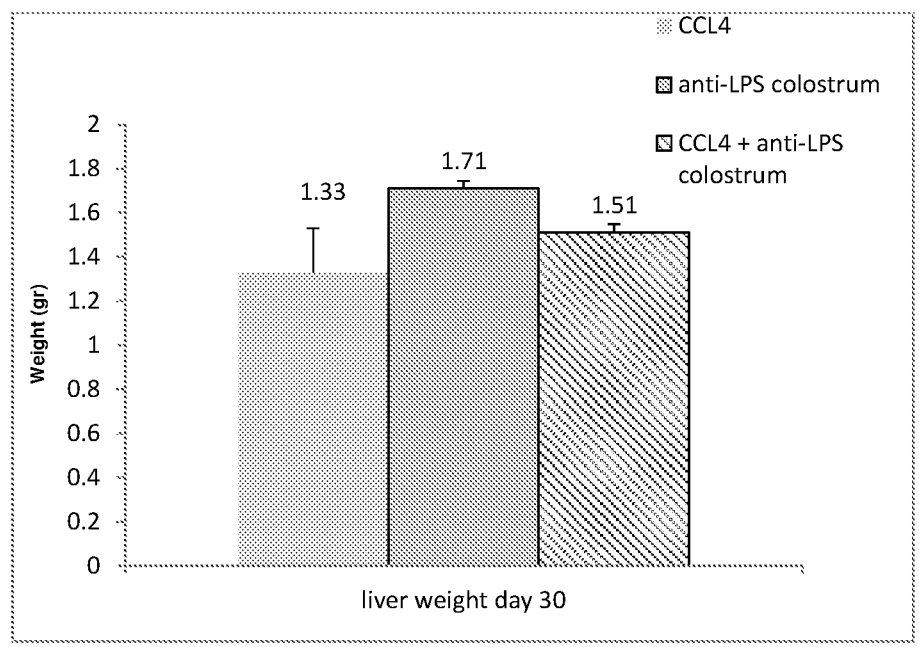
FIG. 2a shows administration of a composition comprising an anti-LPS immunoglobulin-enriched colostrum preparation results in a significant increase in liver weight. The weight in grams of liver samples taken from test mice at day 30 of the trial are shown. Liver weights are on the Y axis. Liver weights are shown to increase in treated mice compared to the weights taken from untreated mice.

FIG. 2a shows administration of a composition comprising an anti-LPS immunoglobulin-enriched colostrum preparation results in a significant increase in liver weight. The weight in grams of liver samples taken from test mice at day 30 of the trial are shown. Liver weights are on the Y axis. Liver weights are shown to increase in treated mice compared to the weights taken from untreated mice.

Figure 2B:
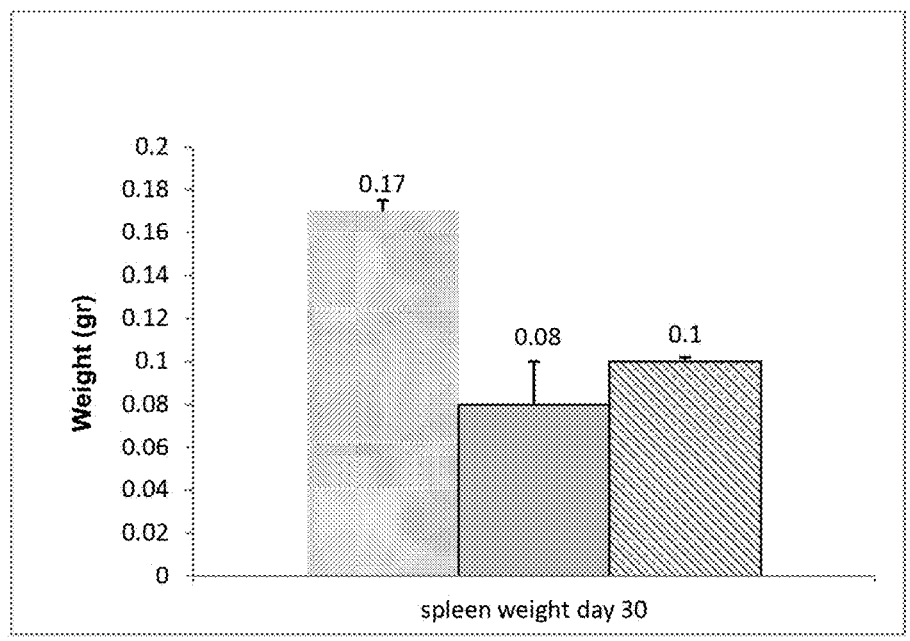
FIG. 2b shows administration of a composition comprising an anti-LPS immunoglobulin-enriched colostrum preparation results in a significant decrease in spleen weight. The weight in grams of spleen samples taken from test mice at day 30 of the trial are shown. Spleen weights are on the Y axis. Spleen weights are shown to decrease in treated mice compared to the weights taken from untreated mice.

FIG. 2b shows administration of a composition comprising an anti-LPS immunoglobulin-enriched colostrum preparation results in a significant decrease in spleen weight. The weight in grams of spleen samples taken from test mice at day 30 of the trial are shown. Spleen weights are on the Y axis. Spleen weights are shown to decrease in treated mice compared to the weights taken from untreated mice.

Figure 2C:
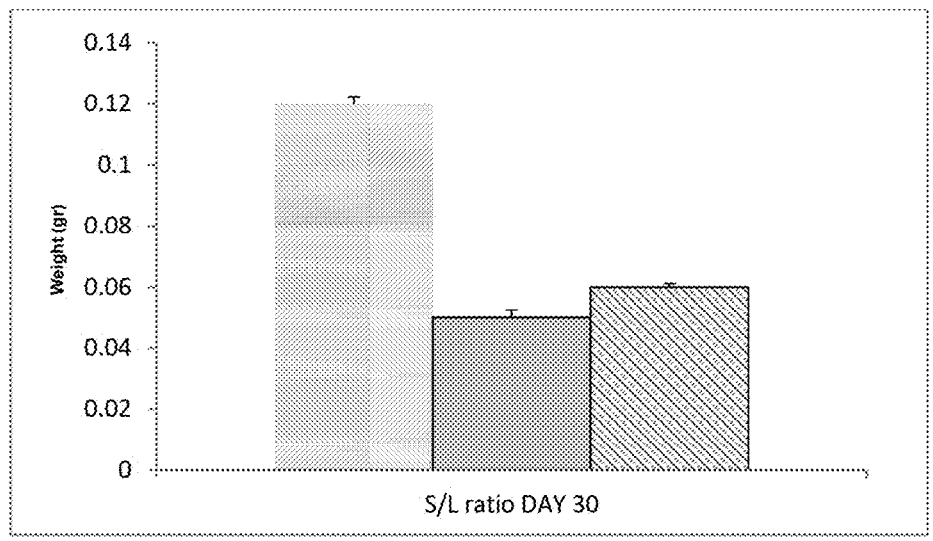
FIG. 2c shows administration of a composition comprising an anti-LPS immunoglobulin-enriched colostrum preparation results in a significant decrease in spleen weight. The weight in grams of spleen to liver ratios in samples taken from test mice at day 30 of the trial is shown. A significant decrease in spleen weight is shown affecting the weight ratio of spleen to liver.

FIG. 2c shows administration of a composition comprising an anti-LPS immunoglobulin-enriched colostrum preparation results in a significant decrease in spleen weight. The weight in grams of spleen to liver ratios in samples taken from test mice at day 30 of the trial is shown. A significant decrease in spleen weight is shown affecting the weight ratio of spleen to liver.

It is considered that the underlying mechanism of these results may be that extensive fibrosis with formation of fibrous septum occurs at the advanced stages of fibrosis. This fibrous septum then may lead to portal congestion and hypertension, obstruction of spleen vein and splenomegaly.

It is also noted that the has been shown that the spleen to liver ratio is significantly different between normal individuals and also between liver cirrhosis patients. In this situation, data indicating that a treatment may be effective for liver cirrhosis is no indication that the same treatment may be effective against liver fibrosis.

Fibrosis Scoring

Fibrosis scoring was performed blindly by professional pathologist. Administration of anti-LPS colostrum caused a significant decrease in periportal necroinflammation changes ($p<0.02$) and portal inflammation ($p<0.02$) as shown in FIGS. 3a and 3b respectively. Anti-LPS colostrum treatment slightly reduced the bridging and confluent necrosis in mice livers (FIG. 3c). FIG. 4a shows that treatment with anti-LPS colostrum significantly reduced the fibrosis score of the liver ($p<0.0009$) quantified by the Metavir fibrosis scoring. Daily treatment with anti-LPS colostrum resulted in overall improvement of fibrosis status of liver as can be seen in H&E (FIG. 5) and trichrome (FIG. 6) staining.

Infiltration of Kuppfer Cells

Kuppfer cells are liver infiltration macrophages. The fibrotic livers contain a large number of infiltrating immune cells. As can be seen in FIG. 7, daily treatment with anti-LPS colostrum reduced the percentage of F4/80 positive cells in the liver as was measured by FACS analysis (FIG. 7a) and by immunohistochemistry quantification (7b).

Oral administration of a composition comprising an anti-LPS immunoglobulin-enriched colostrum preparation exerts an immunomodulatory effect in mice treated with CCl4. Carbon tetrachloride (CCl(4)) is a common hepatotoxin used in experimental models to elicit liver injury. The regulatory effect and suppression of F4/80 macrophages was associated with alleviation liver damage and fibrosis in these treated mice.

Such results are considered surprising in the context of potentially hundreds of molecules contributing to fibrosis, and the labyrinth of interconnections between them. It is further noted that different organs both include and share 'core' and 'regulatory' molecular pathways. Whereas a core pathway is essential to convert an initial stimulus to the development of fibrosis, regulatory pathways are those that can influence the core pathway but do not directly convert the initial stimulus into the basic component of fibrosis. Regulatory pathways may have substantial effects on fibrosis but will also have greater variability between organs, species and individuals, challenging the value of these targets.

References are incorporated herein by this reference.

REFERENCES

Wiest R, Lawson M, Geuking M. J Hepatol. 2013 Aug. 27. pii: S0168-8278(13)00602-8. doi: 10.1016/j.jhep.2013.07.044. Pathological bacterial translocation in liver cirrhosis.

Guarner C, González-Navajas J M, Sánchez E, Soriando G, Francés R, Chiva M, Zapater P, Benlloch S, Muñoz C, Pascual S, Balanzó J, Pérez-Mateo M, Such J. Hepatology. 2006 September; 44(3):633-9. The detection of bacterial DNA in blood of rats with CCl4-induced cirrhosis with ascites represents episodes of bacterial translocation.

Gómez-Hurtado I, Santacruz A, Peiró G, Zapater P, Gutiérrez A, Perez-Mateo M, Sanz Y, Francés R. PLoS One. 2011; 6(7):e23037. doi: 10.1371/journal.pone.0023037. Epub 2011 Jul. 29. Gut microbiota dysbiosis is associated with inflammation and bacterial translocation in mice with 0014-induced fibrosis.

De Minicis S, Rychlicki C, Agostinelli L, Saccomanno S, Candelaresi C, Trozzi L, Mingarelli E, Facinelli B, Magi G, Palmieri C, Marzioni M, Benedetti A, Svegliati-Baroni G. Hepatology. 2013 Aug. 19. doi: 10.1002/hep.26695. Dysbiosis contributes to fibrogenesis in the course of chronic liver injury.

Liu C, Tao Q, Sun M, Wu J Z, Yang W, Jian P, Peng J, Hu Y, Liu C, Liu P. Lab Invest. 2010 December; 90(12):1805-16. doi: 10.1038/labinvest.2010.123. Epub 2010 Oct. 4. Kupffer cells are associated with apoptosis, inflammation and fibrotic effects in hepatic fibrosis in rats.

The invention claimed is:

1. A method of treatment and/or alleviation of fibrosis in a subject having fibrosis, with the proviso that said fibrosis is not a pulmonary fibrosis, the method comprising inhibiting macrophage infiltration into fibrotic tissue by administering to the subject a composition comprising a therapeutically effective amount of an anti-LPS immunoglobulin-enriched colostrum preparation.

2. The method of claim 1, wherein the fibrosis is liver fibrosis, kidney fibrosis, heart blood vessel fibrosis, gastrointestinal tract fibrosis, muscle fibrosis, pancreatic fibrosis, bowel fibrosis, spleen fibrosis, or heart fibrosis.

3. The method of claim 1, wherein macrophage infiltration into the tissue is inhibited by at least 30%.

4. The method of claim 1, wherein the tissue is liver fibrotic tissue or heart fibrotic tissue.

5. The method of claim 1, wherein the immunoglobulin preparation is derived from bovine colostrum or avian eggs.

6. The method of claim 1, wherein the anti-LPS immunoglobulin preparation is administered at a dose of about 100 mg to about 2000 mg per day.

* * * * *